(12) United States Patent
Li et al.

(10) Patent No.: US 9,972,546 B2
(45) Date of Patent: May 15, 2018

(54) ETCHING TIME DETECTION MEANS AND METHOD FOR ETCHING DEVICE (71) Applicant: BEIJING BOE OPTOELECTRONICS TECHNOLOGY CO., LTD., Beijing (CN)

(72) Inventors: Tiansheng Li, Beijing (CN); Changjiang Yan, Beijing (CN); Shaoying Xu, Beijing (CN); Zhenyu Xie, Beijing (CN); Xiaohui Jiang, Beijing (CN)

(73) Assignee: BEIJING BOE OPTOELECTRONICS TECHNOLOGY CO., LTD., Beijing (CN)

( * ) Notice: Subject to any disclaimer, the term of this patent is extended or adjusted under 35 U.S.C. 154(b) by 606 days.

(21) Appl. No.: 13/984,342

(22) PCT Filed: Mar. 12, 2013

(86) PCT No.: PCT/CN2013/072479
§ 371 (c)(1),
(2) Date: Aug. 8, 2013

(87) PCT Pub. No.: WO2013/143389
PCT Pub. Date: Oct. 3, 2013

(65) Prior Publication Data
US 2014/0063503 A1 Mar. 6, 2014

(30) Foreign Application Priority Data

Mar. 31, 2012 (CN) .................... 2012 2 0134133 U (51) Int. Cl.
*H01L 21/67* (2006.01)
*H01L 21/66* (2006.01)
*G01N 21/59* (2006.01)

(52) U.S. Cl.
CPC ............ *H01L 22/10* (2013.01); *G01N 21/59* (2013.01); *H01L 21/67253* (2013.01);
(Continued)

(58) Field of Classification Search
CPC ... H01L 22/12; H01L 22/26; H01L 21/67253; H01L 22/10; H01L 2924/0002;
(Continued)

(56) References Cited

U.S. PATENT DOCUMENTS 5,565,114 A * 10/1996 Saito et al. ...................... 216/60
5,614,026 A * 3/1997 Williams ............... 118/723 ME
(Continued)

FOREIGN PATENT DOCUMENTS

CN 202601580 U 12/2012

OTHER PUBLICATIONS

International Search Report dated Jun. 27, 2013; PCT/CN2013/072479.
(Continued)

*Primary Examiner* — Yuechuan Yu
(74) *Attorney, Agent, or Firm* — Ladas & Parry LLP (57) ABSTRACT

An etching time detection means and an etching time detection method for an etching device. The detection means comprises: a light wave emitter fixed on one substrate of the etching device, a light wave receiver fixed on another substrate and opposed to the light wave emitter, a detection system communicated with the light wave emitter and the light wave receiver for receiving light intensity signals and calculating etching time. With the detection means and the detection method, the automatical detection of etching time can be achieved and the deviation caused by visual observation can be effectively avoided.

9 Claims, 6 Drawing Sheets

(52) U.S. Cl.
CPC ............... H01L 22/12 (2013.01); H01L 22/26 (2013.01); *H01L 2924/0002* (2013.01)

(58) Field of Classification Search
CPC .......... H01L 2924/00; H01L 21/32136; G01N 21/59; H01J 37/32963; H01J 37/32972
See application file for complete search history.

(56) References Cited

U.S. PATENT DOCUMENTS

| | | | |
|---|---|---|---|
| 6,136,719 A * | 10/2000 | Miller et al. | 438/707 |
| 6,261,372 B1 * | 7/2001 | Shimizu | 118/712 |
| 2005/0118737 A1 * | 6/2005 | Takagi | H01J 37/3244 438/14 |
| 2008/0075834 A1 * | 3/2008 | Ramaswamy | C23C 14/48 427/8 |
| 2008/0152840 A1 * | 6/2008 | Ripley et al. | 427/595 |
| 2014/0063503 A1 | 3/2014 | Li et al. | |

OTHER PUBLICATIONS

International Preliminary Report on Patentability Appln. No. PCT/CN2013/072479; dated Oct. 1, 2014.

\* cited by examiner

ETCHING TIME DETECTION MEANS AND METHOD FOR ETCHING DEVICE

TECHNICAL FIELD

The embodiments of the present invention relate to a field of etching technology, and particularly relate to an etching time detection means and an etching time detection method used in an etching device.

BACKGROUND

The present invention relates to an etching device, for example, the etching device used for manufacturing a thin film transistor liquid crystal display (TFT-LCD). Take the etching device used for manufacturing the TFT-LCD as an example, the etching device comprises a storage tank, an inlet chamber, an air knife, a shower, a sample, a sensor, a heating means, a rinse means, and an etching chamber, etc.

The etching chamber is the main location for etching reaction. The etching chamber comprises a first etching chamber, a second etching chamber and a third etching chamber. Wherein, the majority of etching reaction is occurred in the first etching chamber for removing the main film in an etching sample; and then the etching sample is transferred into the second etching chamber for cleaning the residual film of the sample; finally the profile of the pattern is mainly formed in the third etching chamber. The chemical reagents employed in the three etching chamber are the same and are applied by two storage tanks disposed beneath. But the consumption speed of the reagent in the first etching chamber is relative more rapid than those in the second and third etching chambers. The chemical reagent undergone the reaction is flowed back into the storage tanks for reusing, and the chemical reagent should be periodically replaced after it is used for a period of time.

Figure 1:
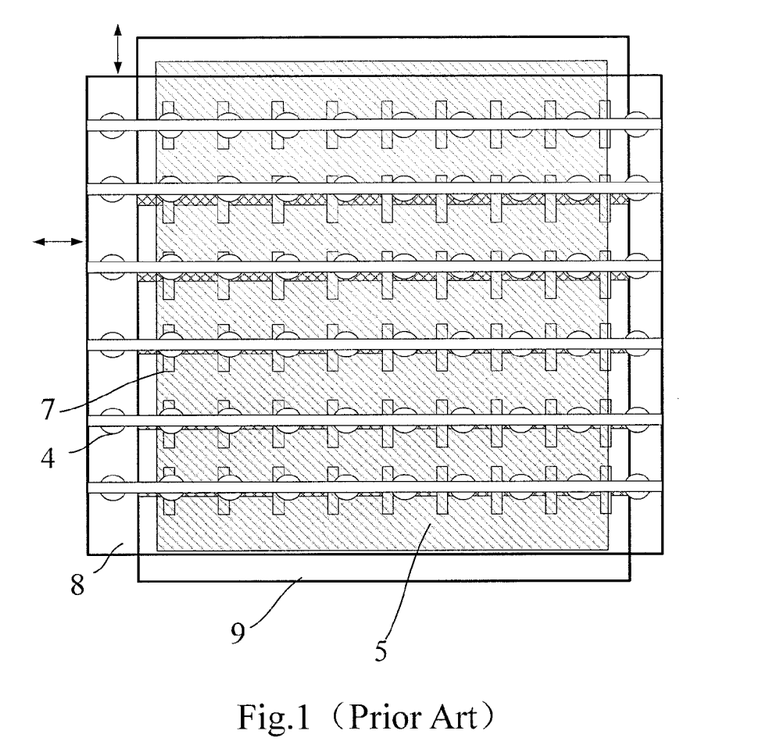
FIG. 1 illustrates a top view of an etching chamber of an etching device in prior art.
Figure 2:
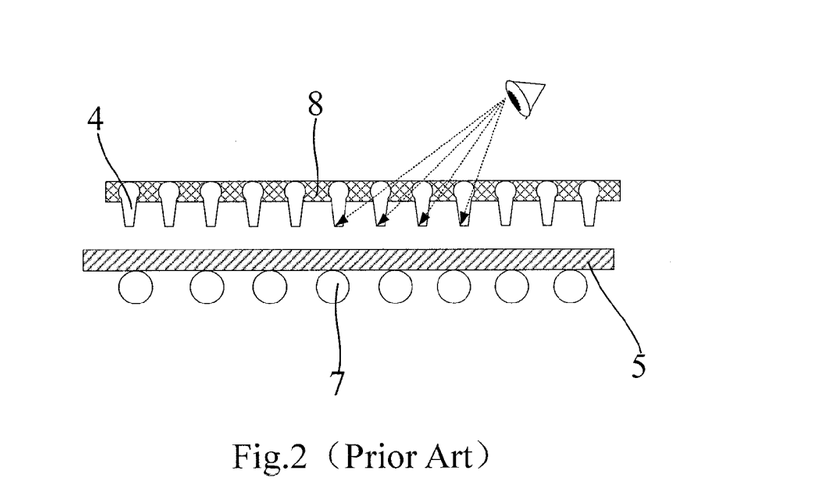
FIG. 2 illustrates a side view of an etching chamber of an etching device in prior art.

FIG. 1 and FIG. 2 schematically illustrate the first etching chamber of the etching device in prior art in a simplified way. FIG. 1 shows a top view, and FIG. 2 shows a side view. As shown in FIG. 1 and FIG. 2, a substrate 5 is transferred into the etching cavity by a transmission apparatus, such that rolling wheels 7. In this case, the substrate 5 is located between an upper substrate 8 and a lower substrate 9 of the etching device, and the etchant sprayed by the nozzles 4 is in contact with the substrate 5 for etching. In prior art, whether the etching is finished that is judged by visual observation, namely the etching time is detected by human eyes (as arrow shown in FIG. 2). When the etchant that has not been reacted is nearly clear with high transmittance. After the substrate 5 is transferred into the etching chamber by the rolling wheels, the etchant is in contact with the substrate and the etching reaction is started, at this time, the etchant becomes turbid and the transmittance is decreased. Simultaneously, the operator starts timing using a stopwatch until the etching reaction is nearly finished and the etchant become clear again, the timing is ended. The period from the time when the etchant becomes turbid to the time when the etchant turns to clear again is defined as the etching time.

The etching time is an important parameter for the subsequent processes. If the detected etching time is shorter than the actual etching time, the residual will be remained after the etching process. If the detected etching time is longer than the actual etching time, an over etching will be occurred. Therefore, the accuracy of detecting the etching time is the most important. As mentioned above, detecting the etching time by visual observation in prior art is not only difficult to achieve an accurate etching time, but also dangerous in operation.

SUMMARY

Embodiments of the present invention provide an etching time detection means and an etching time detection method for an etching device.

According to a first aspect of the present invention, there is provided an etching time detection means for an etching device, comprising:

a light wave emitter fixed on one of a upper substrate and a lower substrate in the etching device for emitting a light wave to an etchant, wherein the upper substrate and the lower substrate are arranged opposed to each other;

a light wave receiver fixed on another substrate of the upper substrate and the lower substrate and opposed to the light wave emitter for receiving the light wave emitted from the light wave emitter and transmitted through the etchant; and a detection system communicated with the light wave emitter and the light wave receiver for receiving the light intensity signals from the light wave emitter and the light wave receiver and calculating the etching time.

According to a second aspect of the present invention, there is provided an etching device comprising the etching time detection means described above.

According to a third aspect of the present invention, there is provided an etching time detection method used with the etching time detection means described above, and the method comprises:

emitting the light wave to an etchant in the etching device;

receiving the light wave transmitted through the etchant; and calculating etching time based on the light intensity signals of the emitted light wave and the transmitted light wave.

BRIEF DESCRIPTION OF THE DRAWINGS

In order to clearly illustrate the technical solution of the embodiments of the invention, the drawings of the embodiments will be briefly described in the following; it is obvious that the described drawings are only related to some embodiments of the invention and thus are not limitative of the invention.

DESCRIPTION OF REFERENCE NUMERALS 1. calculation system 2. light wave emitter 3. light wave receiver 4. nozzle
5. substrate 7. rolling wheel 8. upper substrate of an etching device
9. lower substrate of an etching device 10. fixing screw
101. transmittance calculation module
102. timing start detection module 103. timing end detection module
104. etching time calculation module

DETAILED DESCRIPTION

In order to make objects, technical details and advantages of the embodiments of the invention apparent, the technical solution of the embodiment will be described in a clearly and fully understandable way in connection with the drawings related to the embodiments of the invention. It is obvious that the described embodiments are just a part but not all of the embodiments of the invention. Based on the described embodiments herein, those skilled in the art can obtain other embodiment(s), without any inventive work, which should be within the scope of the invention.

Unless otherwise defined, all the technical and scientific terms used herein have the same meanings as commonly understood by one of ordinary skill in the art to which the present invention belongs. The terms "first," "second," etc., which are used in the description and the claims of the present application for invention, are not intended to indicate any sequence, amount or importance, but distinguish various components. Also, the terms such as "a," "an," etc., are not intended to limit the amount, but indicate the existence of at lease one. The terms "comprises," "comprising," "includes," "including," etc., are intended to specify that the elements or the objects stated before these terms encompass the elements or the objects and equivalents thereof listed after these terms, but do not preclude the other elements or objects. The phrases "connect", "connected", etc., are not intended to define a physical connection or mechanical connection, but may include an electrical connection, directly or indirectly. "On," "under," "right," "left" and the like are only used to indicate relative position relationships, and when the position of the object which is described is changed, the relative position relationship may be changed accordingly.

Referring to FIGS. 3-7, according to an embodiment of the present invention, an etching time detection means comprises a calculation system 1, a light wave emitter 2 and a light wave receiver 3.

Figure 3:
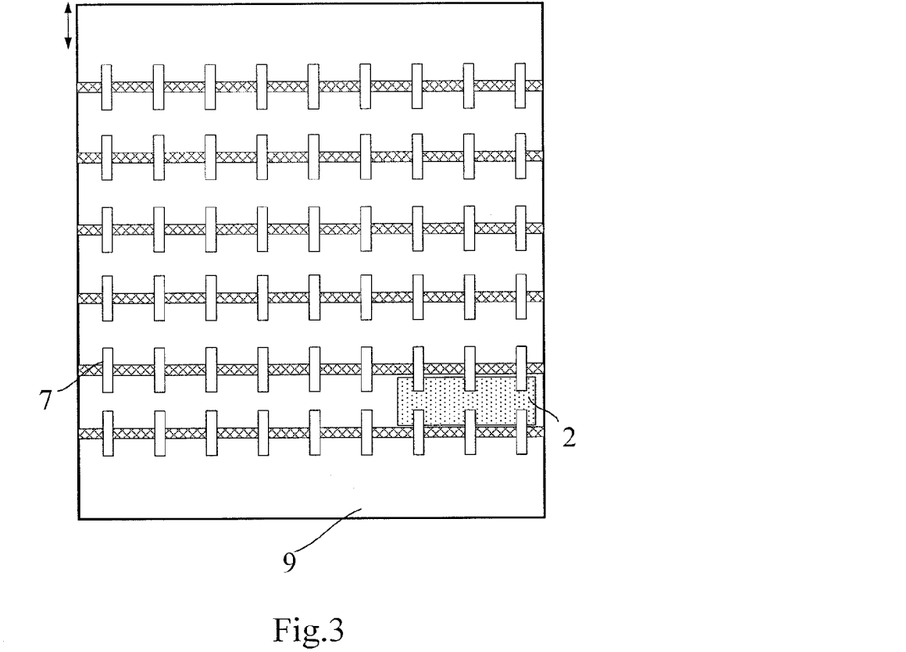
FIG. 3 schematically illustrates a mounting position of a light wave emitter of an etching time detection means on an etching device according to an embodiment of the present invention.
Figure 7:
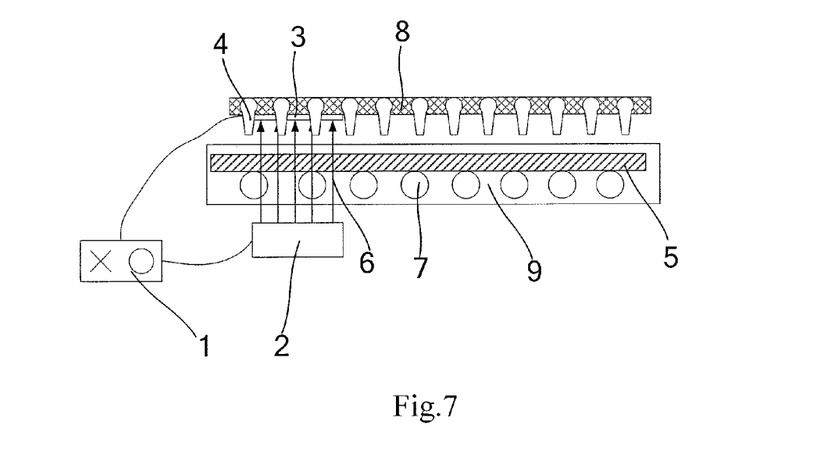
FIG. 7 illustrates a side view of an etching chamber of an etching device mounted with an etching time detection means.

As shown in FIG. 3 and FIG. 7, a plurality of rolling wheels are arranged in an lower substrate 9 of an etching device, the light wave emitter 2 is fixed under the lower substrate 9, namely on the backside of the lower substrate 9 (the front side of the lower substrate faces to the light wave receiver) for emitting light wave to an etchant, that is, the light is upwardly emitted to transmit through the etchant above the substrate 5. The connection between the light wave emitter 2 and the substrate 5 can be mechanical connection (e.g. threaded fastener) or chemical bonding (e.g. adhesive).

As shown in FIG. 3, the light wave emitter 2 can be designed in a rectangle shape, its long side is parallel to the motion direction of the substrate 5, and namely, its long side is perpendicular to the axis of the rolling wheels 7. The shape of the light wave emitter 2 is not limitative in the present invention, but the area of the light wave emitter 2 is preferably greater than the area of the light wave receiver 3 to ensure that if a relative displacement is generated between the upper substrate and the lower substrate, the light wave receiver 3 can still be located in the irradiation region of the light emitted by light wave emitter 2, therefore continuity and availability of the detection can be achieved. In an example, the light wave emitter 2 comprises a light source, a light concentrating system, an aperture, a collimator objective. The light source generally is a filament lamp, a sodium lamp, a mercury lamp, a halogen lamp, etc; the light concentrating system is a collector for improving the utilization of the light source; the aperture is disposed at the focal plane of the collimator objective to generate a parallel light. Preferably, the area of the light wave emitter 2 is greater than the area of the light wave receiver 3, the width of the light wave emitter 2 is typically less than the distance between the rolling wheels on the lower substrate 9 (5 cm), and the length of the light wave emitter 2 is less than the length of the etching chamber (2.5 cm), so that the light wave emitted from the light wave emitter does not be shielded by the rolling wheels, thereby reducing the deviation of the detection.

Figure 4:
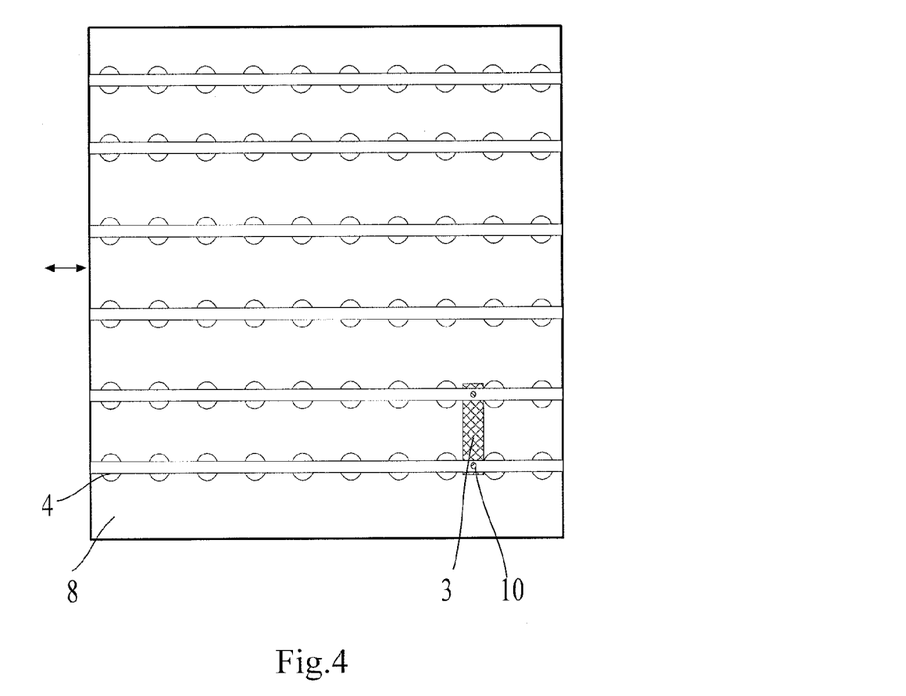
FIG. 4 schematically illustrates a mounting position of a light wave receiver of an etching time detection means on an etching device according to the embodiment of the present invention.

As shown in FIG. 4 and FIG. 7, the light wave receiver 3 is fixed on the upper substrate 8 and opposed to the light wave emitter 2 for receiving and detecting the light intensity signal of the light wave emitted from the light wave emitter 2 and transmitted through the etchant. Preferably, the light wave receiver 3 is arranged in a gap between the nozzles 4 to avoid interferes in the detection result due to that the etchant sprayed from the nozzles 4 spatters the light wave receiver 3. In an example, the light wave receiver 3 comprises a collector, a selenium cell and a phase-locked amplifier. The collector is used for improving the utilization of the light source, the selenium cell is used for receiving and converting the light signal, and the phase-locked amplifier is mainly used for detecting the weak signal synchronized with and in same phase with the reference signal, therefore the noise can be greatly retrained, a signal to noise ratio of the detection can be improved, and the signal can be transferred to the detection system by serial communications. It should be understood that the locations of the light wave receiver 3 and the light wave emitter 2 can be exchanged.

As shown in FIG. 4, the light wave receiver 3 can be designed in a rectangle shape; its long side is perpendicular to the long side of the light wave emitter 2. The light wave receiver 3 is fixed on the upper substrate 8 of the etching device by screws 10. However, the shape of light wave receiver 3 is not limitative in the present invention, but the shape is selected to ensure that the light wave receiver 3 can always receive the light wave emitted from the light wave emitter 2. Simultaneously, it is should taken into account that when a relative displacement is generated between the upper substrate and the lower substrate, the light wave receiver 3 can also receive the light emitted from the light wave emitter 2 to ensure continuity and availability of the detection. In addition, the connection between the light wave receiver 3 and the upper substrate 8 can be achieved by other mechanical connection (e.g. mechanical fastener) or chemical bonding (e.g. adhesive).

Figure 5:
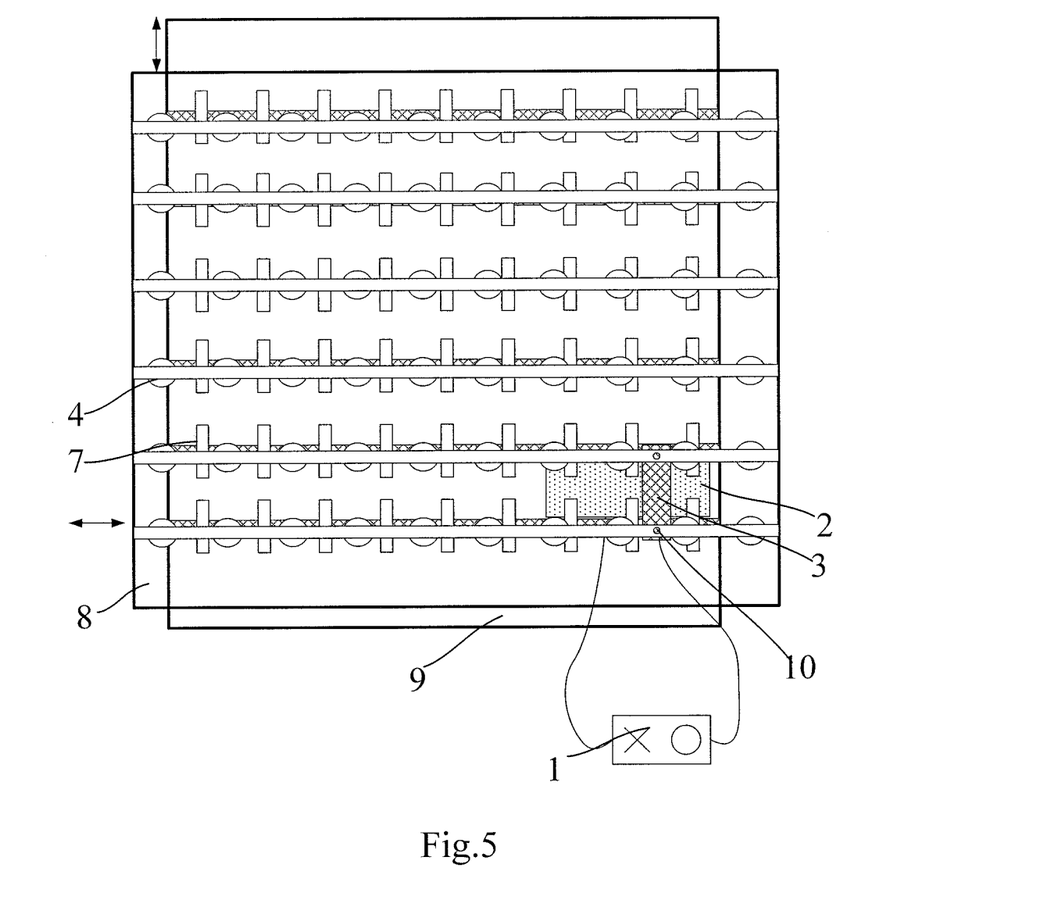
FIG. 5 illustrates the positional relationship between respective components of an etching time detection means and an etching device.
Figure 6:
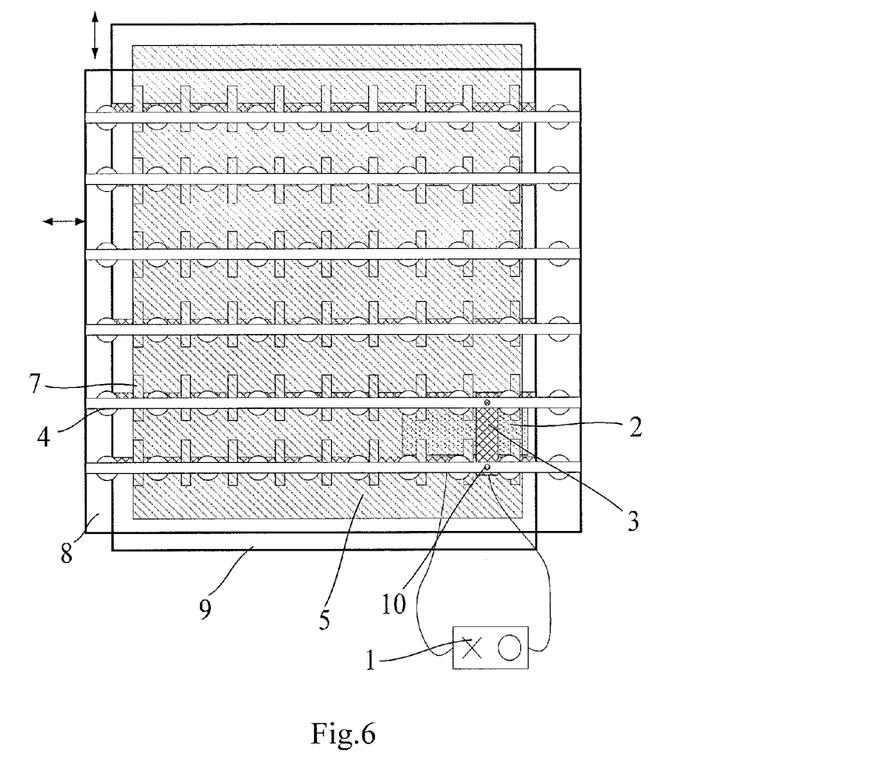
FIG. 6 schematically illustrates a configuration of an etching device according to an embodiment of the present invention when a substrate enters the etching device.
Figure 8:
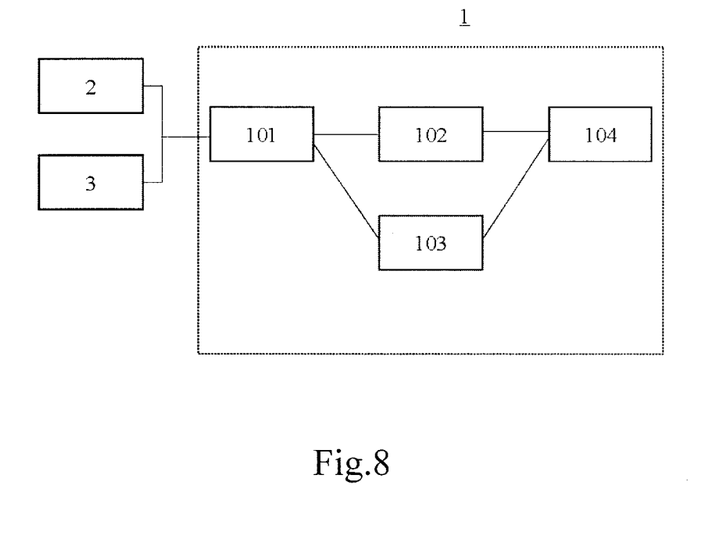
FIG. 8 illustrates a module diagram of an etching time detection means according to an embodiment of the present invention.

As shown in FIGS. 5-7, a detection system 1 is communicated with the light wave emitter 2 and the light wave receiver 3 for receiving light intensity signals from the light wave emitter and the light wave receiver, and then calculating the etching time. Specifically, the detection system 1 detects the transmittance of the light wave transmitted through the etchant, and records etching start time and etching end time based on the detection results, and then calculates the period of etching time, namely, calculates the final detection etching time. As shown in FIG. 8, the detection system 1 may further comprises:

a transmittance calculation module 101, which is communicated with the light wave emitter 2 and light wave receiver 3 for receiving the light intensity signals from the light wave emitter 2 and the light wave receiver 3, and calculating the present transmittance (i.e. the ratio of the light intensity signal received by the light wave receiver 3 to the light intensity signal emitted from the light wave emitter 2) based on the light intensity signals;

a timing start detection module 102, which is communicated with the transmittance calculation module 101 for receiving the transmittance signal sent out by the transmittance calculation module 101, and determining the timing start time (T1) of etching based on the present calculated transmittance and the predetermined first transmittance threshold; for example, the time when the transmittance is decreased to be less than the first transmittance threshold (the etchant is turbid) is defined as T1;

a timing end detection module 103, which is communicated with the transmittance calculation module 101 for receiving the transmittance signal sent out by the transmittance calculation module 101 and determining the timing end time (T2) of etching based on the present calculated transmittance and the predetermined second transmittance threshold; for example, the time when the transmittance is increased to be higher than the second transmittance threshold (the etchant becomes clear again) is defined as T2; the first transmittance threshold is lower than the second transmittance threshold.

an etching time calculation module 104, which is communicated with the timing start detection module 102 and the timing end detection module 103 for calculating the etching time based on T2 and T1.

FIG. 5 is an overall plan view of the etching chamber mounted with the etching time detection means. In the embodiment, by selecting the mounting position, the shape and the area of the light wave emitter 2 and the light wave receiver 3, the light wave receiver 3 can be maintained in the irradiation region of the light wave emitted from the light wave emitter 2, even if the upper substrate and the lower substrate of the etching device are transversely moved, therefore, continuity and availability of the etching time detection can be ensured. As shown in FIG. 5, the light wave emitter 2 and light wave receiver 3 can be respectively connected with calculation system 1 by signal lines.

The principle of the etching time detection according to the embodiment of the present invention is described as follows:

after transferring the substrate 5 into the etching chamber, the etchant is sprayed onto the surface of the substrate by the nozzles. The light wave emitted from the light wave emitter 2 is transmitted to the light wave receiver 3 through the substrate 5 and the etchant. The calculation system 1 receives the light intensity signal emitted from the light wave emitter 2 through the respective signal line between the calculation system 1 and the light wave emitter 2, and receives the light intensity signal received by the light wave receiver 3 through the signal line between the calculation system 1 and the light wave receiver 3, and then the transmittance of the present light wave can be obtained by real time calculation. The time when the transmittance is decreased to reach the predetermined first transmittance threshold is recorded as T1. The time when the transmittance is increased to reach the predetermined second transmittance threshold (from the turbid state to the clear state) is recorded as T2. Then the etching time detection module calculates the etching time (T2−T1).

Figure 9:
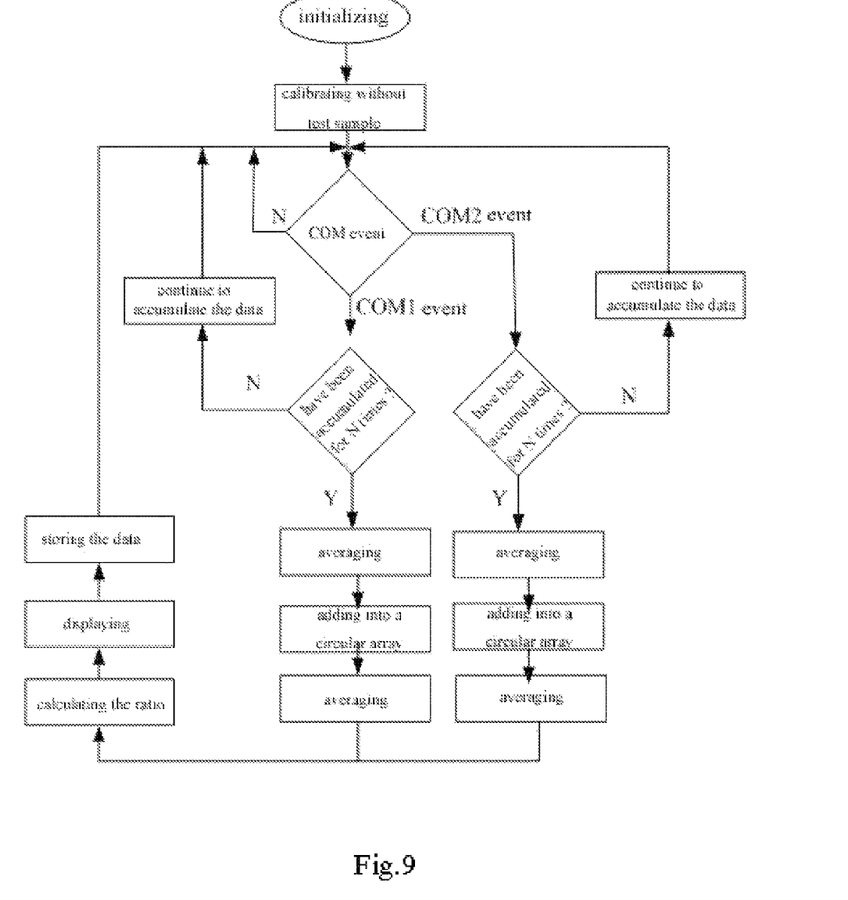
FIG. 9 illustrates a flow chart of signal processing according to an embodiment of the present invention.

FIG. 9 is a flow chart of a signal data according to the embodiment of the present invention. In the example, in processing the light intensity data, components of random noise remained in the data is filtered out by a two-level data filtering method including averaging the values obtained by accumulating for many times and averaging the values obtained by a circular array for improving the accuracy of the detection. In the flow diagram, the process comprises three steps: firstly, calibrating the transmittance without test sample (i.e. calibrating the transmittance before the substrate is transferred into the etching chamber), the value calibrated is the transmittance of the environmental factors, such as the etchant and the air. For example, the situation in which the transmittance value detected without test sample is assumed as 100%, which is defined as COM event. The situation in which the transmittance value is more than 80% is defined as COM1 event. The values are detected at a time intervals set for sampling, and these values are averaged during a time period, then the averaged value is added to a circular array for further averaging. The final real value is displayed on the screen. More particularly, in an example, before the substrate is transferred into the etching chamber, the time interval of sampling can be set as 1 second for once sampling, and three values can be obtained and averaged during 3 seconds. For example, three detected values are 86%, 85% and 84% respectively, thus the average of these values is 85%. During 5 minutes before the substrate is transferred into the chamber, 300 values can be detected and 100 average values can be obtained (certainly, the time period for averaging is not limitative). These 100 average values are added to a circular array, the value displayed on the screen is calculated by averaging 10 average values randomly selected from those 100 average values. Secondly, when the substrate is reacted after transferring into the chamber, the measured transmittance value is resulted from the environmental factors, such as etchant, air and the substrate. In this case, the transmittance value will be obviously decreased caused by the reaction. It is assumed that the situation in which the transmittance value is less than 50% will trigger COM2 event and the timing is started, the principle of the display is same as described above. Finally, when the transmittance value is increased to trigger COM1 event again, the timing is end. Therefore, the time period between the COM1 event and the COM2 event is defined as the etching time of EPD (Electrophoretic Display).

In the embodiment, the etching time detection means comprises one light wave emitter 2 and one light wave receiver 3 opposed to each other. However, in the other embodiments of the present invention, for improving the accuracy of the calculation, it can be provided with a plurality of the light wave emitters and a plurality of the light wave receivers. Therefore, a plurality of the etching times can be calculated, and then the final etching time can be obtained by averaging the plurality of etching times. In addition, in another embodiment of the present invention, the locations of the light wave emitter 2 and the light wave receiver 3 can be exchanged, namely the light wave emitter 2 can be arranged on the upper substrate 8 (the surface facing to the lower substrate), and the light wave receiver 3 can be arranged on the lower substrate 9.

In the present invention, the transmittance detection means is fixed on the upper substrate or the lower substrate in the etching device. The state of the etchant during the chemical reaction is detected by the light transmittance. The time when the transmittance reaches the threshold value is recorded as end time of etching, such that the automatical detection of the etching time can be achieved, the deviation caused by the eye observation can be avoided, and accurate etching time can be obtained. Therefore the process can be optimized and the rate of qualified product can be enhanced.

According to another embodiment of the present invention, there is also provide that a detection method of the etching time by using the etching time detection means described above, the method comprises:

emitting the light wave to the etchant in the etching device;

receiving the light wave transmitted through the etchant; and calculating etching time based on the light intensity signals of the emitted light wave and the transmitted light wave.

In an example, calculating etching time based on the light intensity signals of the emitted light wave and the transmitted light wave comprises: calculating the light transmittance based on the light intensity signal of the emitted light wave and the transmitted light wave.

In an example, calculating etching time based on the light intensity signals of the emitted light wave and the transmitted light wave further comprises: determining the timing start time of etching and the timing end time of etching based on the light transmittance.

In an example, calculating etching time based on the light intensity signals of the emitted light wave and the transmitted light wave further comprises: calculating the etching time based on the timing start time of etching and the timing end time of etching.

In an example, determining the timing start time of etching and the timing end time of etching based on the transmittance further comprises:

predetermining a first transmittance threshold, the time when the light transmittance is decreased to be lower than the first transmittance threshold is defined as the timing start time of etching; and predetermining a second transmittance threshold, the timing end time of etching is defined as the time when the light transmittance is increased to be higher than the second transmittance threshold as the finish time of etching.

In contrast to the detection method in prior art, the etching time detected by the detection method according to the present invention is more reasonable and accurate. This detection method is more convenient and safer to operate and can avoid the deviation caused by visual observation. In addition, because the light transmittance detection means has low cost and it is simple to fix, it is suitable for large-scale production.

What are described above is related to the illustrative embodiments of the disclosure only and not limitative to the scope of the disclosure; the scopes of the disclosure are defined by the accompanying claims.

What is claimed is:

1. An etching time detection means for an etching device including an upper substrate and a lower substrate arranged opposed to each other, the means comprising:
    a light wave emitter for emitting a light wave to an etchant;
    a light wave receiver fixed on the upper substrate and opposed to the light wave emitter for receiving the light wave emitted from the light wave emitter and transmitted through the etchant; and
    a detection system communicated with the light wave emitter and the light wave receiver for receiving light intensity signals from the light wave emitter and the light wave receiver and calculating an etching time,
    wherein the detecting system comprises a transmittance calculation module, the transmittance calculation module is communicated with the light wave emitter and the light wave receiver for receiving the light intensity signals from the light wave emitter and the light wave receiver and calculating a transmittance based on a ratio of the light intensity signal received by the light wave receiver to the light intensity signal emitted from the light wave emitter,
    wherein the detecting system further comprises a timing start detection module, a timing end detection module and an etching time calculation module, wherein
    the timing start detection module is configured for receiving the transmittance output from the transmittance calculation module and determining a timing start time of etching in response to that the transmittance is decreased to be less than a first transmittance threshold;
    the timing end detection module is configured for receiving the transmittance output from the transmittance calculation module and determining a timing end time of etching in response to that the transmittance is increased to be higher than a second transmittance threshold, after the timing start time of etching is determined, wherein, the first transmittance threshold is lower than the second transmittance threshold.

2. The means according to claim 1, wherein the light wave receiver is arranged in such way that the light wave emitted from the light wave emitter is transmitted through the etchant and reaches the light wave receiver.

3. The means according to claim 1, wherein the etching time calculation module is respectively communicated with the timing start detection module and the timing end detection module for calculating an etching time based on the timing start time of etching and the timing end time of etching.

4. The means according to claim 1, wherein a size of the light wave emitter is greater than a size of the light wave receiver in a plan view where the light wave emitter and the light wave receiver are overlapped with each other, the light wave receiver is located within an irradiation region of the light wave emitted from the light wave emitter.

5. The means according to claim 1, wherein a plurality of nozzles are arranged on the upper substrate, the light wave receiver is arranged in a gap between the nozzles.

6. The means according to claim 5, wherein the light wave emitter is arranged on a backside of the lower substrate.

7. The means according to claim 1, wherein the light wave emitter is of a strip shape extending in a first direction, and the light wave receiver is of a strip shape extending in a second direction, the first direction is perpendicular to the second direction.

8. An etching device comprising the etching time detection means according to claim 1.

9. An etching time detection method used with an etching time detection means for an etching device including an upper substrate and a lower substrate arranged opposed to each other, the method comprises:
- emitting a light wave to an etchant in the etching device by a light wave emitter;
- receiving a light wave emitted from the light wave emitter and transmitted through the etchant by a light wave receiver fixed on the upper substrate and opposed to the light wave emitter; and
- receiving light intensity signals from the light wave emitter and the light wave receiver and calculating a transmittance based on a ratio of the light intensity signals received by the light wave receiver to the light intensity signals emitted from the light wave emitter, by a transmittance calculation module communicated with the light wave emitter and the light wave receiver;
- receiving the transmittance output from the transmittance calculation module and determining a timing start time of etching in response to that the transmittance is decreased to be less than a first transmittance threshold, by a timing start detection module;
- receiving the transmittance output from the transmittance calculation module and determining a timing end time of etching in response to that the transmittance Is increased to be higher than a second transmittance threshold after the timing start time of etching is determined, by a timing end detection module, wherein, the first transmittance threshold is lower than the second transmittance threshold;
- calculating an etching time based on the timing start time of etching and the timing end time of etching, by an etching time calculation module.

* * * * *